(12) United States Patent
Teoh

(10) Patent No.: US 9,764,085 B2
(45) Date of Patent: Sep. 19, 2017

(54) CATHETER ASSEMBLIES WITH VALVES AND RELATED METHODS

(71) Applicant: B. BRAUN MELSUNGEN AG, Melsungen (DE)

(72) Inventor: Teng Sun Teoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 122 days.

(21) Appl. No.: 14/591,275

(22) Filed: Jan. 7, 2015

(65) Prior Publication Data

US 2015/0190570 A1    Jul. 9, 2015

Related U.S. Application Data

(60) Provisional application No. 61/924,860, filed on Jan. 8, 2014.

(51) Int. Cl.
*A61M 5/158* (2006.01)
*A61M 25/00* (2006.01)
*A61M 39/06* (2006.01)
*A61M 25/06* (2006.01)

(52) U.S. Cl.
CPC ........ *A61M 5/158* (2013.01); *A61M 25/0009* (2013.01); *A61M 25/0097* (2013.01); *A61M 25/0606* (2013.01); *A61M 39/0606* (2013.01); *A61M 39/0613* (2013.01); *A61M 2039/062* (2013.01); *A61M 2039/0633* (2013.01); *A61M 2039/0673* (2013.01); *Y10T 29/49826* (2015.01)

(58) Field of Classification Search
CPC ............ A61M 25/0028; A61M 39/045; A61M 39/0606; A61M 39/0613; A61M 2039/066; A61M 2039/0072; A61M 2039/0036; A61M 2039/0063; A61M 39/0693; A61M 2039/0279; A61M 2039/0294

See application file for complete search history.

(56) References Cited

U.S. PATENT DOCUMENTS

| 4,673,393 | A |   | 6/1987  | Suzuki et al. |
| 4,960,412 | A | * | 10/1990 | Fink ................ A61M 39/0606 604/167.04 |
| 5,114,408 | A |   | 5/1992  | Fleischhaker et al. |
| 5,405,323 | A |   | 4/1995  | Rogers et al. |
| 5,817,069 | A |   | 10/1998 | Arnett |

(Continued)

*Primary Examiner* — Nathan R Price
*Assistant Examiner* — Justin L Zamory
(74) *Attorney, Agent, or Firm* — Klein, O'Neill & Singh, LLP

(57) ABSTRACT

Needle assemblies with valves and related methods are disclosed. An exemplary needle assembly includes a needle hub with a needle attached to a distal end of the needle hub and a catheter hub having a wall structure defining an interior cavity and a catheter tube extending distally therefrom having the needle projecting through the catheter tube. A valve with a cylindrical walled structure and a disc with a plurality of slits and flaps are located in the interior cavity of the catheter hub in which the cylindrical walled structure defines an open proximal end. A plurality of flexible ribs can be included and connect to an interior wall surface of the cylindrical walled structure and the disc with an actuator disposed inside the interior cavity of the catheter hub and having a distal end sized and shaped to project into the open proximal end of the valve.

24 Claims, 4 Drawing Sheets

(56) References Cited

U.S. PATENT DOCUMENTS

| | | |
|---|---|---|
| 6,352,520 B1 | 3/2002 | Miyazaki |
| 8,357,119 B2 | 1/2013 | Stout et al. |
| 8,361,038 B2 | 1/2013 | McKinnon et al. |
| 8,926,564 B2 | 1/2015 | King et al. |
| 8,932,257 B2 | 1/2015 | Woehr |
| 9,114,231 B2 | 8/2015 | Woehr et al. |
| 2001/0053895 A1 | 12/2001 | Vaillancourt |
| 2004/0210194 A1 | 10/2004 | Bonnette et al. |
| 2008/0108944 A1 | 5/2008 | Woehr et al. |
| 2008/0108976 A1 | 5/2008 | Johnson et al. |
| 2008/0243092 A1* | 10/2008 | Nilsson ............ A61M 25/0606 604/272 |
| 2011/0282286 A1 | 11/2011 | Argentine |
| 2012/0016301 A1 | 1/2012 | Stout |
| 2012/0016302 A1* | 1/2012 | Stout ................ A61M 25/0693 604/122 |
| 2013/0030386 A1 | 1/2013 | Panian et al. |
| 2015/0038910 A1 | 2/2015 | Harding et al. |

\* cited by examiner

CATHETER ASSEMBLIES WITH VALVES AND RELATED METHODS

FIELD OF ART

The disclosed invention generally relates to intravenous (IV) infusion devices or assemblies, including IV catheters. In particular, IV catheter assemblies having a control valve and related methods are discussed.

BACKGROUND

IV catheters are commonly used for a variety of infusion therapies, including infusing fluids into a patient, withdrawing blood from a patient, or monitoring various parameters of the patient's vascular system. Catheters are typically connected to a catheter adapter that accommodates the attachment of IV tubing to the catheter. Blood control catheters include an internal blood control valve that is opened by the insertion of a male Luer or other object into a proximal end of the catheter adapter. Non-limiting examples of blood control valves are disclosed inUnited States Patent Application Publication No. 2011/0046570, filed Aug. 20, 2009, titled "Systems and Methods for Providing a Flushable Catheter Assembly." Thus, following placement of the catheter into the vasculature of a patient, an IV fluid source can be connected to the catheter adapter, opening the blood control valve. Thus connected, fluid from the IV source can begin flow into a patient through the catheter.

Some catheter adapters permit verification of proper placement of the catheter in the blood vessel before fluid infusion begins, such as by providing a flashback chamber of the catheter assembly where a "flashback" of blood can be observed. To confirm flashback in catheter assemblies that do not include a blood control valve, a clinician must manually occlude the vein to prevent undesirable exposure to blood. In contrast, blood control valves can eliminate the need for such manual occlusion, while also reducing the likelihood of blood exposure during catheter placement.

SUMMARY

Aspects of the present disclosure are directed to a needle assembly comprising a needle hub having a needle attached to the distal end of the needle hub, and sized and shaped to extend distally of a catheter tube; a catheter hub having a wall structure defining an interior cavity, the catheter tube extending distally therefrom; a valve comprising a cylindrical walled structure and a disc comprising a plurality of slits defining a plurality of flaps located in the interior cavity of the catheter hub; said cylindrical walled structure defining an open proximal end; a plurality of flexible ribs connected to an interior wall surface of the cylindrical walled structure and the disc; and an actuator disposed inside the interior cavity and having a distal end sized and shaped to project into the open proximal end of the valve.

The needle assembly wherein the plurality of flexible ribs can move from a first position extending radially in generally straight line to a second position where they are compressed and follow a curved path.

The needle assembly can comprise a plurality of raised sections on at least one of the plurality of flaps, extending radially from an interior wall surface of the cylindrical walled structure to a center of the disc.

The needle assembly wherein the plurality of raised sections can bias the flaps back to a closed position.

The needle assembly wherein the plurality of flexible ribs can be located on the plurality of raised sections.

The needle assembly wherein the valve can be secured between two catheter hub elements.

The needle assembly wherein the valve can move from a first position where the valve is open and the actuator is at least partially in an opening defined by the slits to a second position wherein the valve is closed, without the application of any external force.

The needle assembly can comprise a plurality of raised sections on at least one of the plurality of flaps, extending radially from an interior wall surface of the cylindrical walled structure to a center of the disc.

The needle assembly wherein the slits and ribs can be evenly spaced around a circumference of the valve.

Aspects of the present disclosure can further be directed to a needle assembly comprising a needle hub, a needle attached to the distal end of the needle hub, and sized and shaped to extend distally of a catheter tube; a catheter hub having a wall structure defining an interior cavity, the catheter tube extending distally therefrom; a valve comprising a cylindrical walled structure and a disc comprising a plurality of slits defining a plurality of flaps located in the interior cavity of the catheter hub; said cylindrical walled structure defining an open proximal end; a plurality of raised sections on at least one of the plurality of flaps, extending radially from an interior wall surface of the cylindrical walled structure to a center of the disc; and an actuator disposed inside the interior cavity and having a distal end sized and shaped to project into the open proximal end of the valve.

The needle assembly can comprise a plurality of flexible ribs connected to an interior wall surface of the cylindrical walled structure and the disc.

The needle assembly wherein the plurality of flexible ribs can move from a first position extending radially in generally straight line to a second position where they are compressed and follow a curved path.

The needle assembly can comprise a syringe which acts on a proximal end of the actuator, translating the actuator at least partially through the valve.

The needle assembly wherein the plurality of raised sections can bias the flaps back to a closed position.

The needle assembly wherein the plurality of flexible ribs can be located on the plurality of raised sections.

Yet an additional feature of the present disclosure can include a method for manufacturing a needle assembly comprising forming a needle hub; attaching a needle to the distal end of the needle hub, the needle sized and shaped to extend distally of a catheter tube; providing a catheter hub having a wall structure defining an interior cavity, the catheter tube extending distally therefrom; placing a valve comprising a cylindrical walled structure and a disc comprising a plurality of slits defining a plurality of flaps in the interior cavity of the catheter hub; said cylindrical walled structure defining an open proximal end; forming a plurality of raised sections on at least one of the plurality of flaps, extending radially from an interior wall surface of the cylindrical walled structure to a center of the disc; forming a plurality of flexible ribs connected to an interior wall surface of the cylindrical walled structure and the disc; and providing an actuator disposed inside the interior cavity and having a distal end sized and shaped to project into the open proximal end of the valve.

The method wherein the plurality of flexible ribs can have a first position where the plurality of flexible ribs extend radially in generally straight line and a second position where the plurality of flexible ribs are compressed and follow a curved path.

The method wherein the plurality of flexible ribs can be located on the plurality of raised sections.

The method wherein the slits and the plurality of flexible ribs can be evenly spaced around a circumference of the disk.

The method wherein the ribs can extend form the cylindrical wall structure toward the center of the valve and stop short of the center of the valve a distance greater than a radius of an outside diameter of the actuator.

A still further feature of the present disclosure can include a needle assembly comprising: a needle hub with a needle attached to a distal end of the needle hub; a catheter hub having a wall structure defining an interior cavity and a catheter tube extending distally therefrom having the needle projecting through the catheter tube; a valve comprising a cylindrical walled structure and a disc comprising a plurality of slits defining a plurality of flaps located in the interior cavity of the catheter hub; said cylindrical walled structure defining an open proximal end; a plurality of flexible ribs connected to an interior wall surface of the cylindrical walled structure and the disc; and an actuator disposed inside the interior cavity of the catheter hub and having a distal end sized and shaped to project into the open proximal end of the valve.

The needle assembly wherein the plurality of flexible ribs each can have a first configuration in which the flexible rib has a generally linear shape and a second configuration where the flexible rib is compressed and has a curved or undulating shape.

The needle assembly can further comprise a plurality of raised sections located on at least two of the plurality of flaps, said raised section can extend radially from an interior wall surface of the cylindrical walled structure towards a center of the disc.

The needle assembly wherein the actuator can comprise at least two fins or at least two plunger sections.

The needle assembly wherein the plurality of flexible ribs can be located on a plurality of raised sections.

The needle assembly wherein the valve can be secured between two catheter hub elements.

The needle assembly wherein the valve can move from a first position where the valve is open and the actuator is at least partially in an opening defined by the slits to a second position wherein the valve is closed, without application of any external force.

The needle assembly wherein the slits and the flexible ribs can be evenly spaced around a circumference of the valve.

The needle assembly can further comprise a needle guard for covering a needle tip of the needle located proximally of the valve.

A yet further feature of the present disclosure can include a method for manufacturing a needle assembly comprising: forming a needle hub with a needle having a needle tip; forming a catheter hub having a wall structure defining an interior cavity and a catheter tube extending distally therefrom and locating the needle within the catheter tube; placing a valve comprising a cylindrical walled structure and a disc comprising a plurality of slits defining a plurality of flaps in the interior cavity of the catheter hub; said cylindrical walled structure defining an open proximal end and said disc comprising a distal wall surface and a proximal wall surface; forming a plurality of raised sections on the disc extending radially from an interior wall surface of the cylindrical walled structure to a center of the disc; forming a plurality of flexible ribs connected to an interior wall surface of the cylindrical walled structure and the disc; and positioning an actuator inside the interior cavity and having a distal end sized and shaped to project into the open proximal end of the valve.

The method wherein the plurality of flexible ribs can each include a first configuration in which the flexible rib has a generally linear shape and a second configuration where the flexible rib is compressed and has a curved or undulating shape.

The method wherein the plurality of flexible ribs can be located on the plurality of raised sections.

The method wherein the slits and the plurality of flexible ribs can be evenly spaced around a circumference of the disk.

The method of can further comprise at least one raised section on the distal wall surface of the disc.

The method can further comprise a needle guard positioned proximally of the valve.

BRIEF DESCRIPTION OF THE DRAWINGS

These and other features and advantages of the present device, system, and method will become appreciated as the same becomes better understood with reference to the specification, claims and appended drawings wherein:

DETAILED DESCRIPTION

The detailed description set forth below in connection with the appended drawings is intended as a description of the presently preferred embodiments of needle devices or assemblies provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
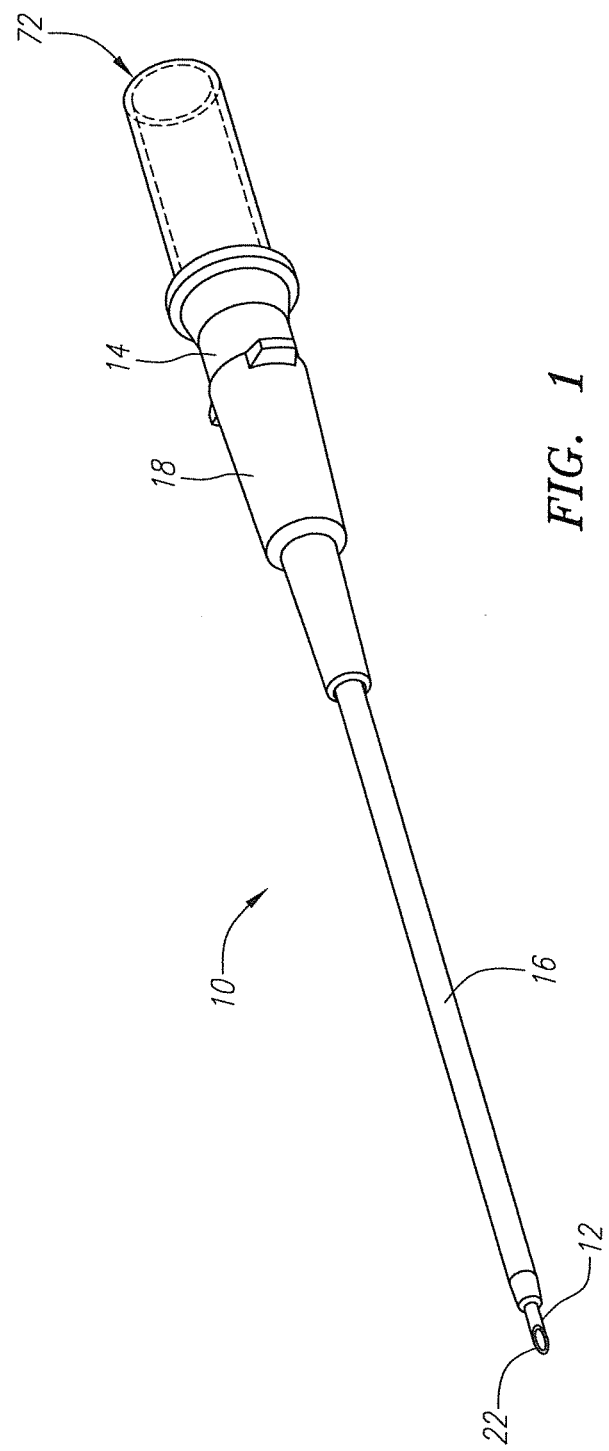
FIG. 1 shows a perspective view of a needle assembly which embodies as a catheter assembly.

FIG. 1 shows one embodiment of a needle assembly 10 comprising a needle 12, a needle hub 14, a catheter tube 16, and a catheter hub 18. The needle 12 has a needle shaft, and a tip 22. Following successful venipuncture, the needle hub 14 is separated from the catheter hub 18, withdrawing the needle 12 from the catheter hub. The catheter tube 16 remains in the punctured vasculature for infusion and/or therapy. When the needle is retracted away from the catheter hub, blood can flow through the catheter tube 16 and into the catheter hub 18. This process is well known in the art and commonly referred to as flashback. Within the catheter hub, a valve (not shown) may be provided to control the flow of fluid through the catheter hub by blocking the path of the fluid. Further, an actuator (not shown) may be provided inside the catheter hub to operate with the valve. The actuator is pushed by a male medical implement to open the valve and allow fluid communication between the catheter tube and the male medical implement, which can be a Luer tip, a syringe tip, or a Luer adaptor for attaching to a female Luer of the catheter hub. The various components disclosed herein may be made with conventional materials unless the context indicates otherwise.

Figure 2:
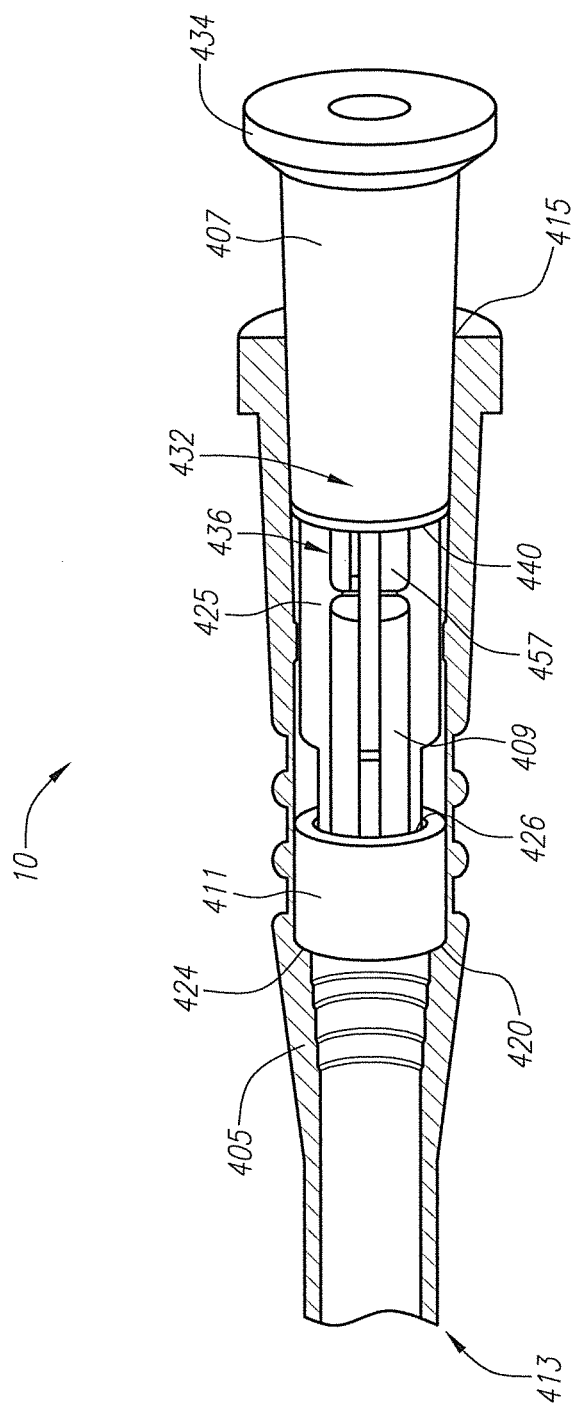
FIG. 2 shows a perspective cross section of an alternative embodiment of a catheter hub with a connector inserted.

FIG. 2 shows another embodiment of a catheter assembly 10 provided in accordance with aspects of the present disclosure. As shown, the catheter assembly 10 comprises a catheter hub 405 having a valve 411 and a valve actuator or opener 409 located in the bore 425 thereof. The catheter assembly 10 is shown without a catheter tube, which is normally attached to a distal end 413 of the catheter hub 405. The catheter assembly 10 is also shown without the needle and needle hub, such as following successful venipuncture and the needle hub and needle have been removed.

A connector 407, such as a syringe tip or a Luer adaptor, is inserted into the open proximal end 415 of the catheter hub 405 to push the actuator 409 in the distal direction into the valve 411. Interiorly, a shoulder 420 is provided to axially locate a distal side 424 of the valve 411 along an axial position within the catheter hub.

The valve 411 has an opening sized and shaped to receive the actuator 409 on its proximal side 426. When the actuator 409 is advanced distally forward as shown in FIG. 2 by the connector 407, the distal end or push end of the actuator 409 forces through the slits 820 (FIG. 4B) at the disc of the valve 411 to deflect the flaps formed by the slits in the axial and radial outward direction. Once the flaps are opened by the actuator, fluid can flow thereacross and fluid communication is provided between the various components when the valve is in the open position.

A distal end 432 of the connector 407, such as a syringe tip or a male Luer adaptor, contacts the actuator 409 at a proximal end 436 of the actuator 409. For example, the end surface 440 of the connector tip or Luer tip abuts spaced apart plunger or pusher elements 457 on the actuator 409 to advance the distal end of the actuator into the skirt section of the valve 411. In one example, two or more pusher elements 457 are provided, such as four spaced apart pusher elements connected to one another by one or more ribs or connectors. The space or spaces around the pusher elements and the one or more ribs provide flow paths for fluids discharged from the connector 407. The connector 407 is shown with a flared base 434, which is understood as a schematic representation of any number of structures or components that can have a male Luer tip, such as a syringe or a Luer adaptor connected to a tubing line. Due to the construction of the valve 411, discussed in detail hereinafter, pressure applied by the connector 407 causes the valve 411 to open, such as forcing the distal end of the actuator 409 to open the valve, placing the connector 407 in fluid communication with the catheter hub 405, and in turn, the catheter tube 16 (FIG. 1) and ultimately a patient (not shown).

Figure 3:
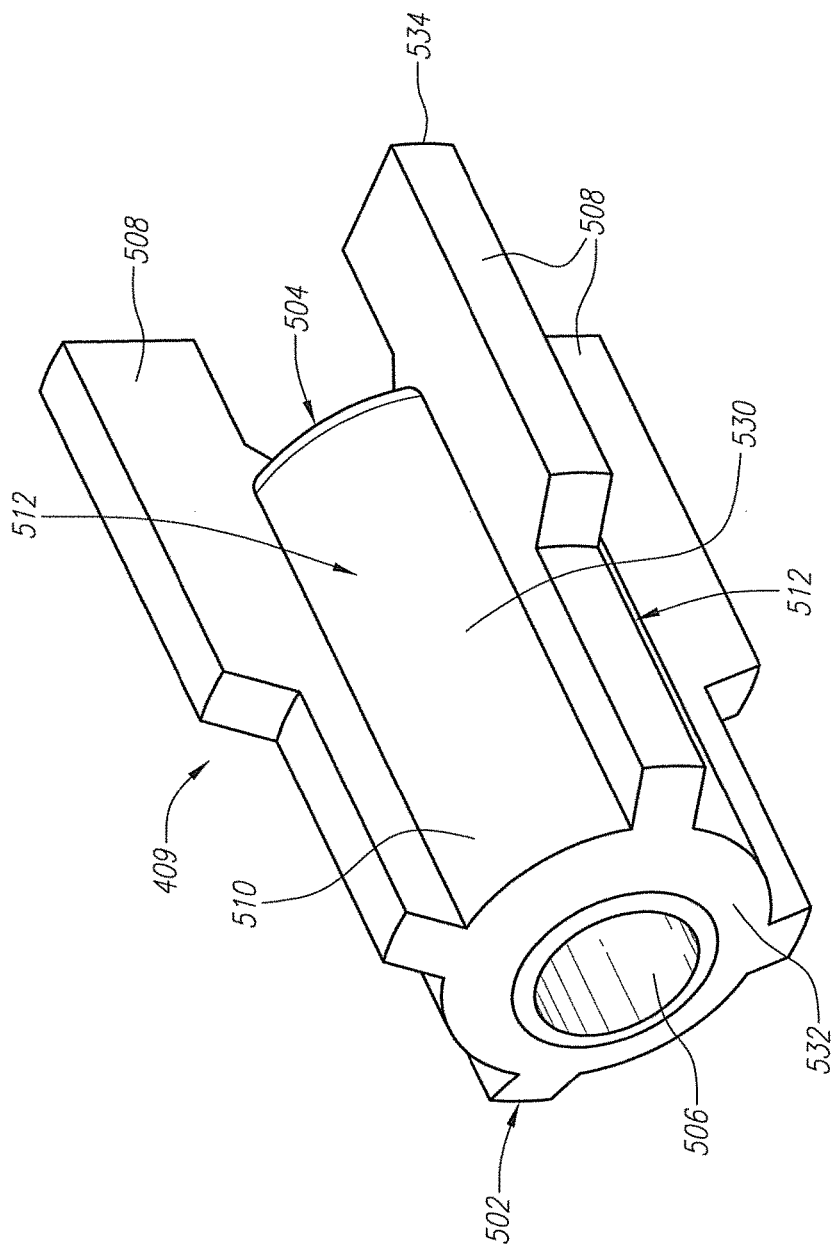
FIG. 3 shows a perspective view of one embodiment of an actuator.

FIG. 3 is a detailed perspective view of an exemplary actuator 500 provided in accordance with aspects of the present disclosure. The actuator 500 of the present embodiment comprises a body 530 having a distal end 502 and a proximal end 504 with a lumen 506 extending therebetween. A plurality of fins 508 emanate radially from the exterior or outer surface 510 of the body from the distal end 502 of the actuator 500 to and past the proximal end 504 of the body 530. In one example, the fins 508 are evenly spaced around the outer surface 510 of the actuator 500 to form flow channels or paths 512 on the outer surface of the actuator. Thus, when a connector pushes the actuator 500 at the proximal end 534 of the fins and discharges fluid through the catheter hub, fluid flow can flow between the fins 508 along the plurality of flow paths 512, through the lumen 506, or both. In some embodiments, the fins are of an equal radial depth along their lengths. In other embodiments, as shown, they have different radial depths with one or more transitions in between. In still other embodiments, the fins taper radially outward from the distal end to the proximal end of the actuator. The portions of the fins 508 that extend past the proximal end 504 of the body 510 form contact points for the connector 407 (FIG. 2) to act on. The present actuator 500 may be used with any of the catheter hubs and valves discussed elsewhere herein.

Figures 4A, 4B, 4C:
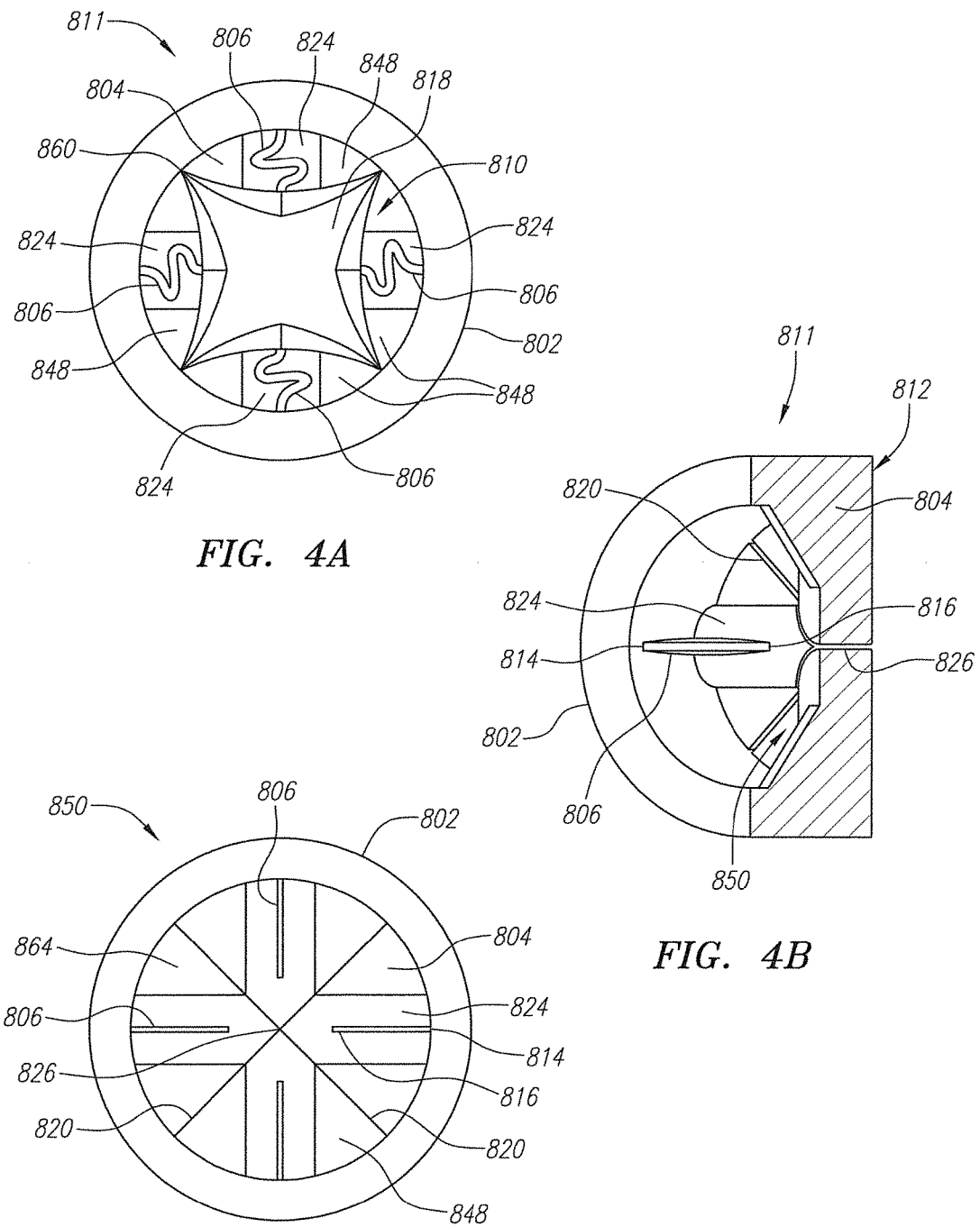
FIG. 4A shows a detailed plan view of an embodiment of a valve in the open position.
FIG. 4B shows a detailed cross section perspective view of the valve of FIG. 4A in a closed position.
FIG. 4C is an end view of the valve of FIG. 4A, looking at the proximal surface of the disc.

FIGS. 4A and 4B show a valve 811 in accordance with aspects of the present disclosure in detail. The valve 811 is usable with a single hub body catheter hub (FIGS. 1 and 2) or a two-part hub body catheter hub (not shown) and with any number of actuators, such as the actuators described herein. As shown, the valve 811 comprises a cylindrical walled portion or skirt 802 defining an interior 810 and a disc 804 at a distal end 812 of the cylindrical walled portion 802. The disc 804 has a proximally facing surface and a distally facing surface. The valve 811 may be understood as a cylinder valve having a combination skirt and disc. The disc 804 has a thickness that can be uniform or non-uniform. One or more slits 820 are formed through the disc 804, such as through the thickness of the disc, to define two or more flaps 848. The flaps are independently movable due to the slits cutting or forming through the thickness of the disc. In one example, at least one of the slits 820 extends through the disc 804 and radially to the intersection 860 between the disc and the skirt. In other examples, the at least one slit extends short of the intersection 860. As shown, two slits 820 in the shape of an "X" are provided to form four flaps 848 and wherein the ends of each of the two slits extend to the intersection 860. The slits 820 may also be viewed as having four slit sections that intersect at a center 826 to define four flaps 848. In other examples, the ends of the slits extend short of the intersection between the disc and the skirt. However, other slit configurations including the number of slits and radial spacing of the slits are contemplated. The slits can also be evenly spaced or un-evenly spaced around the circumference of the disc. Moreover, the slit arrangements can vary, such having a Y-shape or a narrow X-shape. The flaps 848, which are formed in the spaces between the slits 820, are deflectable by an actuator, such as one of the actuators discussed elsewhere herein. The tip of the actuator is sized and shaped to at least partially project through the disc at the slits, which forms an opening for accommodating the tip of the actuator. When the actuator enters the slits, the tip of the actuator deflects the flaps 848 to open fluid communication between the connector 407 (FIG. 2) used to move the actuator and the catheter tube. As shown in FIG. 4A, when the flaps 848 are deflected axially and radially, the opening or aperture 818 formed thereby is almost a square shape. As shown, an actuator may open the flaps from the proximally facing surface side of the disc. In other examples, the valve 811 is rotated so that the interior 810 defined by the skirt 802 faces the distal direction. Where this arrangement provided, the actuator opens the flaps 848 from the side of the disc 804 without the skirt 802.

With reference to FIG. 4C in addition to FIGS. 4A and 4B, on a proximal side 850 of the disc 804, one or more raised sections 824 radiate outward from a center 826 of the wall surface of the disc. The raised sections 824 are provided to add thickness and rigidity to the disc 804, and specifically to the flaps 848 between the slits 820. In some embodiments there may be as many raised sections 824 as there are flaps. The raised sections 824 can each resemble a speed bump or a partial elongated cylinder. In other embodiments there may be more than one raised section 824 on one or more of the flaps 848. In still other embodiments, one or more flaps 848 may not have any raised sections. Thus, rather than the "+" configuration for the raised sections shown, the raised sections can form a "┬" shape in which only some of the flaps have a raised section. In the embodiment shown in FIGS. 4A-4C, one raised section 824 per flap 848 is provided. As shown, the raised sections are formed on the flaps 848 with the raised sections placed on the flaps evenly spaced between the slits 820 with un-even spacing contemplated. Also as shown, the slits 820 bi-sect the raised sections 824 so that at the center 826 of the disc 804, the raised sections each has an arrow tip. However, the raised sections 824 can be placed differently on the disc and the slits do not have to bi-sect the raised sections.

One or more flexible ribs 806 are formed on the interior of the circumferential walled portion 802 of the skirt 802. In the embodiment shown, four flexible ribs 806 are provided, one for each flap 848. However, various numbers of flexible ribs 806 are contemplated for each flap and the flaps can have less than a full complement of flexible ribs, including zero flexible rib. In some embodiments, the flexible ribs 806 are each connected to a corresponding raised section 824. In other embodiments, the one or more ribs connect to the circumferential walled portion 802 and the proximal wall surface 864 of the disc, away from the raised sections 824. In other embodiments, the flexible ribs 806 may be provided at other locations, such as touching an edge of a raised section. For example, in the embodiment shown, the flexible ribs 806 are aligned with the raised sections 824 and the flexible ribs 806 are thus spaced equally around the interior 810 of the circumferential walled portion 802. In other embodiments, the flexible ribs 806 may be attached directly to the disc 804. In still other embodiments, regardless of where the flexible ribs are attached, the flexible ribs 806 may be placed in irregular patterns. In some embodiments, the flexible ribs 806 are triangular with the base 814 of the triangular body connected to the circumferential walled portion 802 and the tip end 816 of the triangle closer to the center 826 than the base 814. The base 814 can extend partially up the wall surfaces of the skirt 802 or all the way to the proximal edge of the skirt. The tip end 816 can extend partially along the length of the flap 848 or all the way to the center 826 of the disc. In other embodiments, the flexible ribs 806 may have other shapes, such as squares, rectangles, or any other regular or irregular polygon allowing attachment to the valves discussed elsewhere herein. The thickness of the flexible ribs 806 may also vary to control the elasticity of the ribs. With a relatively thicker flexible rib 806, the ability of the flap to bend is reduced but the ability of the flap to uncoil after the actuator is removed is increased.

As shown in FIG. 4A, the flexible ribs 806 are deflected and/or deformed with the slits 820 spread to open the central aperture 818 of the disc with an actuator. As shown, the flaps 848 are deflected into the interior 810 of the skirt 802, such as by an actuator. The flaps are therefore understood to be deflected by an actuator from the side of the disc 802 without the skirt 802. As previously mentioned, the flaps 848 can also be deflected in the opposite direction, such as away from the interior of the skirt. Upon removal of the connector 407 (FIG. 2) or syringe after opening the flaps, the elasticity of the flexible ribs 806 and the raised sections 824 will cause the flaps to naturally return to their uncompressed or un-deflected state (FIG. 4B) and will push the actuator (not shown) in the proximal direction to allow the flaps to close, as shown in FIG. 4B. This natural bias aids in pushing the actuator (not shown) out of the aperture 818 upon removal of the constraint provided by the connector 407 (FIG. 2), and further aids in sealing the aperture 818 from fluid or leakage. In some examples, the raised sections 824 may be provided on the distal wall surface of the disc 804 while the flexible ribs 806 are provided on the proximal side of the disc inside the interior 810 of the valve 811, such as attaching to the proximal wall surface of the disc 804 and the interior wall surface of the skirt 802.

With reference again to FIGS. 4A and 4B, the flexible ribs are shown having a first configuration in which the flexible ribs each has a generally linear shape when in a relaxed state, such as when the flaps are in the closed position shown in FIG. 4B. When the valve is opened and the flaps are pushed axially and radially, the flexible ribs each has a second configuration where the flexible rib is compressed and has a curved or undulating shape, such as that shown in FIG. 4A. It is understood that the present valve 811 may be used in any of the catheter hubs and with any of the actuators of any of the needle assemblies discussed herein and catheter assemblies in which a hub has an interior cavity with a valve seat for positioning the valve 811 therein.

Thus, aspects of the present disclosure are understood to comprise a catheter assembly comprising a catheter hub with a catheter tube and a needle hub with a needle projecting through the catheter hub and the catheter tube. The catheter hub has an interior cavity having a valve located therein and a valve opener or actuator for opening the valve. Optionally a needle guard is incorporated to cover the needle tip upon removal of the needle from the catheter tube and catheter hub. The valve can have a skirt or a cylindrical walled structure attached to a disc, which has a wall with a proximal wall surface, a distal wall surface, and a depth or thickness. A plurality of slits are provided through the depth of the disc to define a plurality of flaps. In an example, the slits extend from a middle area of the disc to an intersection between the disc and the skirt. In other examples, the slits extend short of the intersection. One or more raised sections may be provided on the proximal wall surface or the distal wall surface of the disc. Optionally, one or more raised sections are provided on the proximal wall surface and on the distal wall surface of the disc. The raised sections, which can embody a partial cylinder structure, can be located on the disc at a location away from the slits and having only small sections located at or near the slits. The raised sections can extend to the intersection between the disc and the skirt or short of the intersection so that they are located only on the disc surface or surfaces. The raised sections increase the firmness and rigidity of the flaps to facilitate the uncoiling of the flaps to a closed position after they are pushed by the actuator. The depth or thickness of the disc may also be adjusted depending on the number of raised sections incorporated and the size, shape, and thickness of the raised sections so that the overall configuration of the disc promotes opening and closing of the flaps.

In addition to the raised sections, flexible ribs may be incorporated on the proximal side of the valve, in a space defined by the skirt and the disc. In some examples, the flexible ribs each comprises a base and a tip end. The base is attached to an interior surface of the skirt and can extend partially along the length of the skirt or up to an even with a proximal edge of the skirt. Less preferably, the base can extend past the proximal edge of the skirt. The tip end of each flexible skirt can extend the longest radial dimension of a flap or short of that dimension. Each flexible rib can be located directly over a raised section, on an edge of a raised section, or on the proximal wall surface of the disc away from a raised portion. The flexible ribs can have a number of shapes, including a triangle, a square, or a triangle with a curved edge. In some examples, the valve comprises a plurality of flexible ribs attached to the skirt, such as an interior wall surface of the skirt, and the disc but without any raised sections on the disc. When the valve is positioned inside a catheter hub and the skirt faces the proximal opening, the valve actuator can contact the flexible ribs before contacting the flaps or the raised sections to push the flaps open. Various valve openers or actuators may be used to open the flaps on the valve. The actuators can have multiple flow paths or a single lumen centrally positioned in the body thereof.

Methods of making and of using the catheter assemblies and components described herein are contemplated.

Although limited embodiments of catheter assemblies and their components have been specifically described and illustrated herein, many modifications and variations will be apparent to those skilled in the art. Furthermore, it is understood and contemplated that features specifically discussed for one catheter assembly may be adopted for inclusion with another catheter assembly, provided the functions are compatible. For example, the valve may be configured differently having more or fewer flaps. Accordingly, it is to be understood that the catheter assemblies and their components constructed according to principles of the disclosed devices, systems, and methods may be embodied other than as specifically described herein. The disclosure is also defined in the following claims.

What is claimed is:

1. A needle assembly comprising:
   a needle hub having a distal end;
   a needle attached to the distal end of the needle hub;
   a catheter hub having a wall structure defining an interior cavity;
   a catheter tube extending distally of the catheter hub, the needle projecting through the catheter tube;
   a valve located in the interior cavity of the catheter hub, said valve comprising a cylindrical walled structure and a disc formed with the cylindrical walled structure, said cylindrical walled structure comprising an exterior wall surface and an interior wall surface defining an interior space, said disc comprising a plurality of slits formed through a thickness of the disc and defining a plurality of flaps, said cylindrical walled structure defining an open proximal end;
   a plurality of flexible ribs connected to the interior wall surface of the cylindrical walled structure and to the disc; and
   an actuator disposed inside the interior cavity of the catheter hub and having a distal end sized and shaped to deflect the plurality of flaps of the disc radially and axially when the actuator is pushed by a male tip inserted into the interior cavity of the catheter hub.

2. The needle assembly of claim 1, wherein the plurality of flexible ribs each has a first configuration in which the flexible rib has a generally linear shape and a second configuration where the flexible rib is compressed and has a curved or undulating shape.

3. The needle assembly of claim 1, further comprising a plurality of raised sections connected to at least two of the plurality of flaps, said plurality of raised sections extending radially from the interior wall surface of the cylindrical walled structure towards a center of the disc.

4. The needle assembly of claim 1, wherein the actuator comprises at least two fins or at least two plunger sections.

5. The needle assembly of claim 2, wherein the plurality of flexible ribs are connected to a plurality of raised sections.

6. The needle assembly of claim 1, wherein the valve is secured between two catheter hub elements.

7. The needle assembly of claim 1, wherein the valve moves from a first position where the valve is open and the actuator is at least partially in an opening defined by the slits to a second position wherein the valve is closed, without application of any external force.

8. The needle assembly of claim 1, further comprising a plurality of raised sections connected to at least two of the plurality of flaps and to at least two of the plurality of flexible ribs.

9. The needle assembly of claim 1, further comprising a needle guard for covering a needle tip of the needle located proximally of the valve.

10. A method for manufacturing a needle assembly comprising:
    forming a needle hub with a needle having a needle tip;
    forming a catheter hub having a wall structure defining an interior cavity and a catheter tube extending distally of the catheter hub, and locating the needle within the catheter tube;
    placing a valve in the interior cavity of the catheter hub, said valve comprising a cylindrical walled structure and a disc formed with the cylindrical walled structure, said cylindrical walled structure comprising an exterior wall surface and an interior wall surface defining an interior space, said disc comprising a plurality of slits formed through a thickness of the disc and defining a plurality of flaps, said cylindrical walled structure defining an open end located opposite the disc and said disc comprising a distal wall surface and a proximal wall surface;
    forming a plurality of flexible ribs connected to the interior wall surface of the cylindrical walled structure and to the disc; and
    positioning an actuator inside the interior cavity of the catheter hub, said actuator comprising a distal end sized and shaped to project through the plurality of slits of the disc.

11. The method of claim 10, wherein the plurality of flexible ribs each has a first configuration in which the flexible rib has a generally linear shape and a second configuration where the flexible rib is compressed and has a curved or undulating shape.

12. The method of claim 11, wherein the plurality of flexible ribs are connected to plurality of raised sections.

13. The method of claim 12, wherein the plurality of slits and the plurality of flexible ribs are evenly spaced around a circumference of the disc.

14. The method of claim 13, further comprising at least one raised section on the distal wall surface of the disc.

15. The method of claim 13, further comprising a needle guard positioned proximally of the valve.

16. A needle assembly comprising:
    a catheter hub having a wall structure defining an interior cavity;
    a catheter tube extending distally of the catheter hub;
    a needle hub having a distal end;

a needle attached to the distal end of the needle hub, said needle projecting through the catheter tube;

a valve located in the interior cavity of the catheter hub, said valve comprising a cylindrical walled structure and a disc formed with the cylindrical walled structure, said cylindrical walled structure comprising an exterior wall surface, an interior wall surface defining an interior space, and an open end located opposite the disc, said disc comprising a plurality of slits formed through a thickness of the disc and defining a plurality of flaps;

a plurality of flexible ribs connected to the interior wall surface of the cylindrical walled structure;

a plurality of raised sections extending outwardly from a wall surface of the disc having at least one of the slits located between two raised sections or cutting through one of the raised sections; and an actuator disposed inside the interior cavity of the catheter hub and having a distal end sized and shaped to deflect the flaps of the disc when the actuator is pushed by a male tip inserted into the interior cavity of the catheter hub.

17. The needle assembly of claim 16, wherein the wall surface of the disc has a proximally facing wall surface and a distally facing wall surface and wherein the plurality of raised sections are formed on the proximally facing wall surface of the disc.

18. The needle assembly of claim 16, wherein the wall surface of the disc has a proximally facing wall surface and a distally facing wall surface and wherein the plurality of raised sections are formed on the distally facing wall surface of the disc and spaced from the plurality of flexible ribs.

19. The needle assembly of claim 16, wherein the plurality of flexible ribs are connected to the plurality of raised sections.

20. The needle assembly of claim 16, wherein the actuator comprises at least two fins or at least two plunger sections.

21. The needle assembly of claim 16, wherein the distal end of the actuator is located in the open end of the cylindrical walled structure to deflect the plurality of flaps.

22. The needle assembly of claim 16, wherein the distal end of the actuator contacts the disc on a side of the valve away from the cylindrical walled structure.

23. The needle assembly of claim 17, wherein the plurality of slits and the plurality of flexible ribs are evenly spaced around a circumference of the valve.

24. The needle assembly of claim 16, further comprising a needle guard for covering a needle tip of the needle located proximally of the valve.

* * * * *

UNITED STATES PATENT AND TRADEMARK OFFICE
CERTIFICATE OF CORRECTION

PATENT NO. : 9,764,085 B2
APPLICATION NO. : 14/591275
DATED : September 19, 2017
INVENTOR(S) : Teng Sun Teoh Page 1 of 1

It is certified that error appears in the above-identified patent and that said Letters Patent is hereby corrected as shown below:

In the Specification

In Column 1, Line 22, delete "inUnited" and insert -- in United --, therefor.

In Column 4, Line 16, after "method" delete "of".

In the Claims

In Column 10, Line 55, in Claim 12, before "plurality" insert -- a --.

Signed and Sealed this
Eleventh Day of December, 2018

Andrei Iancu
*Director of the United States Patent and Trademark Office*